United States Patent [19]

Suzuki et al.

[11] 4,321,212

[45] Mar. 23, 1982

[54] METHOD FOR PREPARING AN OPTICALLY ACTIVE α-CYANO-3-PHENOXYBENZYL 2-(4-SUBSTITUTED-PHENYL)ISOVALERATE

[75] Inventors: Yukio Suzuki, Toyonaka; Masachika Hirano, Ibaraki; Koichi Aketa, Kawanishi, all of Japan

[73] Assignee: Sumitomo Chemical Company Limited, Osaka, Japan

[21] Appl. No.: 247,035

[22] Filed: Mar. 24, 1981

[30] Foreign Application Priority Data

Mar. 24, 1980 [JP] Japan .................................. 55-38014

[51] Int. Cl.$^3$ .......................................... C07C 121/75
[52] U.S. Cl. ................................. 260/465 D; 424/304
[58] Field of Search ..................................... 260/465 D

[56] References Cited

U.S. PATENT DOCUMENTS 4,062,968 12/1977 Fujimoto et al. ................... 424/275
4,133,826 1/1979 Warnant ......................... 260/465 D
4,176,195 11/1979 Stoutamire ......................... 424/304
4,199,595 4/1980 Berkelhammer et al. .......... 424/304
4,238,406 11/1980 Suzuki et al. ................... 260/465 D
4,273,727 6/1981 Martel et al. .................... 260/465 F
4,279,924 6/1981 Suzuki et al. ....................... 424/304

FOREIGN PATENT DOCUMENTS 2289 6/1979 European Pat. Off. .
50-25544 3/1975 Japan .
2001964 2/1979 United Kingdom .
2014137 8/1979 United Kingdom .
1560303 2/1980 United Kingdom .

*Primary Examiner*—Dolph H. Torrence
*Attorney, Agent, or Firm*—Sughrue, Mion, Zinn, Macpeak and Seas

[57] ABSTRACT

A method for preparing an optically active α-cyano-3-phenoxybenzyl 2-(4-substituted-phenyl)-isovalerate, which consists substantially of or is rich in (S)-α-cyano-3-phenoxybenzyl (S)-2-(4-substituted-phenyl)isovalerate.

11 Claims, No Drawings

METHOD FOR PREPARING AN OPTICALLY ACTIVE α-CYANO-3-PHENOXYBENZYL 2-(4-SUBSTITUTED-PHENYL)ISOVALERATE

This invention relates to a process for preparing an optically active α-cyano-3-phenoxybenzyl 2-(4-substituted-phenyl)isovalerate of the formula (I):

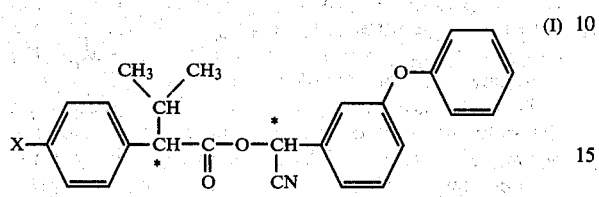

wherein X is a methoxy group which may be unsubstituted or substituted with a fluorine atom or atoms, or an ethoxy group which may be unsubstituted or substituted with a fluorine atom or atoms, and * indicates an asymmetric carbon atom, which contains at least 60% of a compound of said formula having an (S)-configuration on both the acid and alcohol moieties, i.e., an (S)-α-cyano-3-phenoxybenzyl (S)-2-(4-substituted-phenyl)isovalerate.

α-Cyano-3-phenoxybenzyl 2-(4-substituted-phenyl)isovalerates of the formula (I) are useful as insecticides and/or acaricides as disclosed in, for example, U.S. Pat. Nos. 4,062,968 and 4,199,595. These esters have one asymmetric carbon atom on each of the acid and alcohol moieties. An ester provided by the conventional method is a mixture comprising substantially equal amounts of four isomers.

These optical isomers are hereunder referred to as shown in Table 1 below.

TABLE 1

| | Abbreviations for Optical Isomers | | |
|---|---|---|---|
| | | Acid Moiety | |
| Alcohol Moiety | (S)-Configuration | Racemic | (R)-Configuration |
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

However, no single optical isomer which is optically active on both the acid and alcohol moieties has yet been synthesized, and as a matter of course, the relationship between the physiological activity and configuration has not been known.

As a result of syntheses of these optical isomers and review of the physiological activity thereof, the inventors have found that the Aα-isomer, i.e., an ester of the formula (I) having an (S)-configuration on both the acid and alcohol moieties has strong insecticidal and/or acaricidal activity and they have found an economical process for preparing the same, such leading to the accomplishment of this invention.

Of the optical isomers of the esters of the formula (I), the Aα-isomer has the strongest insecticidal and/or acaricidal efficacy which is on the order of about four times greater than that of "racemate" prepared by the conventional method. This fact was first revealed by the inventors and it is very important to understand the fact in controlling various harmful insects and/or mites.

This invention also provides an ester of the formula (I) having an (S)-configuration on the acid moiety, which is rich in the Aα-isomer (hereinafter, this compound being referred to as "Aα rich-isomer"). The biological activity of this ester generally increases in proportion to the content of the Aα-isomer. Such ester has economic advantages over a substantially pure Aα-isomer.

One method of producing the Aα-isomer is by chromatography of a carboxylic ester of the formula (I) having an (S)-configuration on the acid moiety.

An α-cyano-3-phenoxybenzyl 2-(4-substituted-phenyl)isovalerate of the formula (I) having an (S)-configuration on the acid moiety is prepared by esterifying an S-(+)-2-(4-substituted-phenyl)isovaleric acid or a derivative thereof by a known method. The optically active carboxylic acid can be prepared by reacting the carboxylic acid in the racemic form with an optically active amine, followed by optical resolution of the reaction product as disclosed in, for example, Japanese Patent Publication (unexamined) Nos. 25544/75 and 135742/79.

The Aα-isomer may also be prepared via the following route (such being substantially the same as the method disclosed in Japanese Patent Publication (unexamined) No. 59646/78):

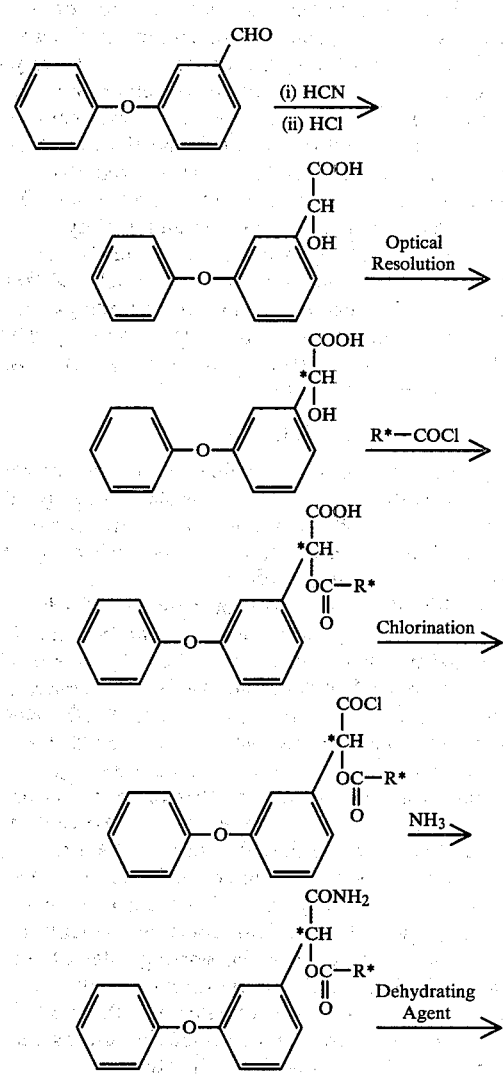

-continued

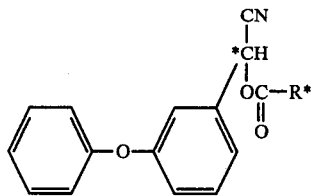

wherein R* is a group represented by the formula

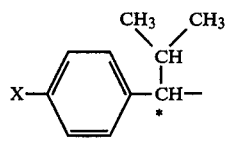

(wherein X has the same meaning as defined above), and * indicates an asymmetric carbon atom.

The Aα-isomer may further be prepared by esterifying (S)-α-cyano-3-phenoxybenzyl alcohol, which is prepared by a method as disclosed in Japanese Patent Publication (unexamined) Nos. 109944/79 and 130557/79, with an S-(+)-2-(4-substituted-phenyl)isovaleric acid or a derivative thereof.

However, these conventional methods are complicated and are not always suitable on an industrial scale.

Therefore, the inventors continued to extensively study processes for preparing optically active esters of the formula (I) and found that the Aα-isomer can be crystallized. The inventors further found that the Aα-isomer crystal can be selectively crystallized from a solution of the corresponding ester of the formula (I) having an (S)-configuration on the acid moiety (i.e., A-isomer) and that the presence of a basic catalyst in the crystallization system helps increase the yield of the Aα-isomer crystal greatly. Based on these findings, the inventors have established a process for producing the optically active ester of this invention very advantageously on an industrial scale.

Method (A)

The process comprises crystallizing an Aα-isomer from a solution of an ester of the formula (I) having an (S)-configuration on the acid moiety in the presence or absence of a basic catalyst, followed by separation of the crystal from the mother liquor.

If this process is effected in the absence of a basic catalyst, the ester recovered from the mother liquor which contains an increased amount of the Aβ-isomer is brought into contact with a basic catalyst to epimerize it on the alcohol moiety. After the ratio of the Aα-isomer to the Aβ-isomer reaches substantially equilibrium, the crystallization is further conducted whereby the ester of the formula (I) having an (S)-configuration on the acid moiety can be converted to the Aα-isomer almost quantitatively. On the other hand, if the process is effected in the presence of a basic catalyst, it becomes possible to obtain the crystal of the Aα-isomer in an amount higher than that initially contained (usually in an amount of about 50%) in the starting ester of the formula (I) having an (S)-configuration on the acid moiety. In this case, the ester remaining in the mother liquor may be recovered and purified for use as the starting material for the next crystallization.

Method (B)

Alternatively, the crystal of the Aα-isomer is crystallized from the ester of the formula (I) having an (S)-configuration on the acid moiety in the presence of a basic catalyst, the basic catalyst is removed or inactivated (or neutralized) without separating the crystal from the mother liquor, and the whole is then subjected to concentration or other conventional procedures to recover the ester of the formula (I) having an (S)-configuration on the acid moiety together with the crystal of the Aα-isomer whereby the Aα rich-isomer is obtained.

This alternative method is more advantageous from the industrial and economical standpoints because it permits effective use of the Aα-isomer remaining in the mother liquor without losing it and is a simpler operation. Furthermore, if desired, the Aα rich-isomer may be recrystallized to provide the Aα-isomer of higher purity.

In any of the methods described above, it is preferred that the starting ester of the formula (I) having an (S)-configuration on the acid moiety desirably is in the racemic form on the alcohol moiety, but in the presence of a basic catalyst, any proportion of the (S)-configuration to the (R)-configuration on the alcohol moiety may be used. It is preferred that the optical purity on the acid moiety is 80% or more, preferably 90% or more.

In the process of this invention, since the ester used as the starting material is a liquid which is hardly fluid at the crystallization temperature, a solvent is generally used. Any solvent may be used without particular limitation so long as it dissolves therein the A-isomer or the Aβ-isomer to a moderate extent and has a sufficiently low solubility to the Aα-isomer. Examples of the solvent are aliphatic hydrocarbons, e.g., hexane, heptane, etc., alicyclic hydrocarbons, e.g., methylcyclohexane, etc., lower alcohols, e.g., methanol, ethanol, etc., and mixed solvents containing the same. Of these, the lower alcohols are preferred, particularly methanol. The concentration of the starting ester in the solution can be freely selected from the range of 1 to 95 wt%, preferably 20 to 80 wt%.

Crystallization of the Aα-isomer is preferably performed by seeding with crystals. The seed crystal which can be used is preferably the crystal of the Aα-isomer of the corresponding ester. There is no particular limitation on the amount of the seed crystals used, and the use of a high amount of seed crystals generally results in rendering the more efficient crystallization. The crystallization of the Aα-isomer can be carried out continuously or semicontinuously. In this case, the seeding with crystals may be effected only at the initiation of crystallization of the Aα-isomer.

Examples of the basic catalyst include nitrogen-containing bases such as ammonia, hydrazine, methylamine, ethylamine, n-propylamine, isopropylamine, n-butylamine, dimethylamine, diethylamine, di-n-propylamine, di-n-butylamine, trimethylamine, triethylamine, cyclohexylamine, ethylenediamine, ethanolamine, pyrrolidine, piperidine, morpholine, aniline, 1-naphthylamine, pyridine, quinoline, 1,5-diazabicyclo[4,3,0]-none-5-ene, etc., phosphorus-containing bases such as triphenylphosphine, tri-n-butylphosphine, etc., quaternary ammonium hydroxides such as tetramethylammonium hydroxide, tetra-n-butylammonium hydroxide, etc., metal-containing bases such as sodium hydroxide, potassium hydroxide, sodium carbonate, sodium cyanide, sodium methylate, sodium hydride, sodium amide, talc, bentonite, etc., basic ion exchange resins, and the like, with the ammonia and triethylamine being preferred.

The proportion of the catalyst to the starting ester may be freely selected from the range of from 0.001 mol% to 100 mol%, preferably from 1 mol% to 100 mol%, if the catalyst is a weak base such as nitrogen-containing and phosphorus-containing bases, etc. Strong bases such as quaternary ammonium hydroxide, sodium hydroxide, potassium hydroxide, sodium hydride, etc., are desirably used in an amount not greater than 10 mol% to prevent significant decomposition of the ester.

Theoretically, a crystallization temperature lower than the melting point of the desired A$\alpha$-isomer may be used, but the process of this invention is generally performed at a temperature lower than the melting point by about 20° C. and preferably at $-30°$ C. to 0° C.

The process for preparing the compound according to this invention are hereunder described in greater detail by reference to the following examples which are given here for illustrative purposes only and are by no means intended to limit the invention.

In the examples, the ratio of the A$\alpha$-isomer to the A$\beta$-isomer was analyzed by gas chromatography.

EXAMPLE 1

To 1.79 g of S-(+)-2-(4-methoxyphenyl)-isovaleric acid (optical purity: 96.8%) was added 0.67 g of a 49.1% sodium hydroxide aqueous solution, and 5 cc of water, 5 cc of toluene and 0.06 g of tetrabutylammonium bromide were added to the mixture. The resulting mixture was stirred at 60° C., and 2.25 g of $\alpha$-bromo-3-phenoxyphenyl acetonitrile dissolved in 10 cc of toluene was then dropwise added thereto. After completion of the dropwise addition, the mixture was further stirred at 70° C. for 3 hours.

The aqueous layer thus formed was separated, and the oily layer was washed successively with 5 cc of a 10% sodium carbonate aqueous solution and 10 cc of water. The oily layer thus treated was concentrated in vacuo to obtain 3.23 g of $\alpha$-cyano-3-phenoxybenzyl S-(+)-2-(4-methoxyphenyl)isovalerate (A-isomer).

$[\alpha]_D^{23} -5.54°$ (chloroform, C=2); $n_D^{23.5}$ 1.5623.

EXAMPLE 2

0.5 g of $\alpha$-cyano-3-phenoxybenzyl S-(+)-2-(4-methoxyphenyl)isovalerate (A-isomer) was dissolved in 1 g of methanol. Then, the resulting solution was allowed to stand for 2 days at $-25°$ C. During this procedure, crystals were found to gradually precipitate. The thus-formed crystals of (S)-$\alpha$-cyano-3-phenoxybenzyl S-(+)-2-(4-methoxyphenyl)isovalerate (A$\alpha$-isomer) were collected by filtration.

Yield 0.12 g.
m.p. 60° to 62° C.

EXAMPLE 3

3 g of $\alpha$-cyano-3-phenoxybenzyl S-(+)-2-(4-methoxyphenyl)isovalerate (A-isomer) was dissolved in 6 g of methanol, and the solution was cooled to $-15°$ C. After 0.50 cc of an 8.4% ammonia-methanol solution and 10 mg of the crystal as a seed crystal of the A$\alpha$-isomer of the ester were added thereto, the mixture was stirred at the same temperature for 24 hours. Thereafter, 1.0 cc of 10% aqueous hydrochloric acid, 10 cc of toluene and 10 cc of water were added to the reaction system, and the resulting mixture was thoroughly stirred. The aqueous layer thus-formed was separated. The oily layer was washed twice with 10 cc of water, and then concentrated in vacuo to obtain 2.95 g of the A$\alpha$ rich-isomer of the ester.

A$\alpha$-isomer/A$\beta$-isomer=76/24.
$n_D^{23}$ 1.5616.

EXAMPLE 4

600 mg of $\alpha$-cyano-3-phenoxybenzyl S-(+)-2-(4-difluoromethoxyphenyl)isovalerate (A-isomer) was dissolved in hexane, and the solution was adsorbed on a silica gel column (Lobar Column, Size B Lichroprep Si 60, a product of Merck & Co.) and eluted with a mixed solvent of hexane and ethyl acetate (100:1 vol/vol). The A$\alpha$-isomer component which was checked by gas chromatography was collected and concentrated in vacuo to obtain 142 mg of the A$\alpha$-isomer of the ester.

m.p. 48° to 50° C.
$[\alpha]_D^{21} -7.84°$ (chloroform, C=1.73).

EXAMPLE 5

3 g of $\alpha$-cyano-3-phenoxybenzyl S-(+)-2-(4-difluoromethoxyphenyl)isovalerate $[[\alpha]_D^{22} -5.51°$ (chloroform, C=5.05)] was dissolved in a mixed solvent of 6 g of heptane and 3 g of methanol, and the solution was cooled to $-20°$ C. After 10 mg of the crystal as a seed crystal of A$\alpha$-isomer of the ester and 0.50 cc of an 8.4% ammonia-methanol solution were added thereto, the mixture was stirred at $-20°$ C. for 24 hours. Thereafter, 1.0 cc of 10% aqueous hydrochloric acid, 10 cc of toluene and 10 cc of water were added to the reaction system, and the resulting mixture was thoroughly stirred. The aqueous layer thus-formed was separated. The oily layer was washed twice with 10 cc of water, and then concentrated in vacuo to obtain 2.90 g of the A$\alpha$ rich-isomer of the ester.

A$\alpha$-isomer/A$\beta$-isomer=85.4/14.6.
$[\alpha]_D^{21} -5.02°$ (chloroform, C=1.83).
$n_D^{23}$ 1.5398.

The compounds according to this invention are highly effective as insecticides and/or acaricides in controlling the below-illustrated harmful insects on field crops, fruit trees, vegetables, forests and woodwork, insanitary insects and harmful insects on livestock, exhibit a high insecticidal and/or acaricidal activity and residual activity against these harmful insects, and have low toxicity to mice, rats and other mammals. For this reason, there is no particular limitation on the field where the compound of this invention can be used with advantage.

1. Order Hemiptera:
   white-backed planthopper, smaller brown planthopper, brown planthopper, green rice leafhopper, grain aphid, green peach aphid, cotton aphid, cabbage aphid, common green stink bug, azalea lacewing bug, citrus whitefly
2. Order Lepidoptera:
   peach leaf miner, tea leaf roller, apple leaf miner, citrus leaf miner, diamond-back moth, summer fruit tortrix, tea tortrix, rice stem borer, grass leaf roller, corn borer, pine moth, tent caterpillar, akebia leaf-like moth, armyworm, cabbage armyworm, tobacco cutworm
3. Order Coleoptera:
   striped flea beetle, daikon leaf beetle, rice leaf beetle, rice plant weevil, adzuki bean weevil, cupreous chafer, soybean beetle
4. Order Diptera:

yellow fever mosquito, anopheles mosquito, common mosquito, housefly, onion maggot, green bottle fly, flesh fly, rice leaf miner 5. Order Orthoptera:
short-winged rice grasshopper
6. Order Isoptera:
Formosan subterranean termite, Japanese termite
7. Order Blattoidea:
German cockroach, American cockroach, smoky brown cockroach
8. Order Acarina:
carmine mite, two-spotted spider mite, sugi spider mite, citrus red mite, European red mite, Japanese citrus rust mite, cyclamen mite, cattle tick The optically active compounds of this invention may usually be applied to the field in the form of a formulation using a suitable carrier and/or a diluent. Any desired formulation such as an emulsifiable concentrate, a wettable powder, a dust, a granule, a fine granule, an oil, an aerosol, a thermal fumigant (e.g., mosquito coil, an electric mosquito repellent, etc.), a spray such as fogging, a non-thermal fumigant, and poisonous bait may be made of the compounds of this invention without requiring a special condition and in accordance with the method familiar to the skilled in the art of manufacture of general pyrethroids. The formulations prepared may be used in various applications depending on the purpose.

The insecticidal and/or acaricidal activity of the compounds of this invention may also be enhanced by mixing it with known synergists for pyrethroids, such as α-[2-(2-butoxyethoxy)ethoxy]-4,5-methylenedioxy-2-propyltoluene (hereinafter referred to as piperonylbutoxide (PBO)), etc. If desired, a suitable amount of an antioxidant, a UV absorber, or a stabilizer may further be incorporated into the compounds of this invention to make a stabler composition.

Multipurpose compositions may be prepared or synergistic effect may be provided by combining the compound of this invention with other physiologically active substances, such as insecticides, acaricides, fungicides, nematocides, herbicides, plant growth regulators, fertilizers, microbiological pesticides, insect hormones and other pesticides.

The compound of this invention may be incorporated in an insecticidal and/or acaricidal composition in an amount which preferably ranges from 0.001% to 80%, more preferably from 0.01% to 50%.

The high insecticidal and/or acaricidal efficacy of the compound of this invention is hereinafter described in detail by the following illustrative formulation examples and test examples.

TABLE 2

| Compound No. of this Invention | Structure ["X" in the formula (I)] | Isomer | Example No. |
|---|---|---|---|
| (1) | $CH_3O-$ | A-Isomer | 1 |
| (2) | $CH_3O-$ | Aα Rich-Isomer | 3 |
| (3) | $CH_3O-$ | Aα-Isomer | 2 |
| (4) | $HCF_2O-$ | Aα-Isomer | 4 |
| (5) | $HCF_2O-$ | Aα Rich-Isomer | 5 |

FORMULATION EXAMPLE 1

0.2 part of each of the compounds of this invention, (1), (2), (3), (4) and (5), was dissolved in kerosine to make a total weight of 100 parts to thereby provide a 0.2% oil.

FORMULATION EXAMPLE 2

20 parts of each of the compounds of this invention, (1), (2), (3), (4) and (5), was mixed with 10 parts of Sorpol 3005x (a registered trademark of Toho Chemical Co., Ltd.) and 70 parts of xylene, and the mixture was thoroughly stirred to provide a 20% emulsifiable concentrate.

It will be demonstrated by the following test examples that the thus-formulated insecticides and acaricides of this invention exhibit a high efficacy.

In the following test examples, the "racemate" (conventional product) of each of the compounds of the formula (I) was formulated in the same procedures as in each test example and then used as a reference compound.

Reference Compound (a): a compound of the formula (I) wherein X is a methoxy group (b): a compound of the formula (I) wherein X is a difluoromethoxy group

TEST EXAMPLE 1

Each of the emulsifiable concentrates prepared from the compounds of this invention, (4) and (5), in the procedures described in Formulation Example 2 was diluted with water to a pre-determined concentration, and mixed with 3,000 times by weight based on the diluted solution of a spreader (Shin-Rino, a registered trademark of Nippon Noyaku Co., Ltd., for a mixture containing 20% of an alkylphenol polyethylene glycol ether and 12% of a salt of lignin sulfonic acid).

Leaves were cut from a cabbage plant (prior to the head) cultivated in a flower pot, dipped in the above solution for 1 minute and air-dried. The dried leaves were placed in plastic cups (diameter 10 cm, height 4 cm) at a rate of 2 leaves/cup, and the fourth instar larvae of tobacco cutworms were liberated therein. The dead and alive was evaluated after 24 hours and the values of $LC_{50}$ (concentration required for 50% death) were obtained.

Experiments of three replications were carried out using 10 larvae per group. The results are shown in Table 3.

TABLE 3

| Compound | $LC_{50}$ (ppm) |
|---|---|
| Compound (4) | 5.9 |
| Compound (5) | 6.9 |
| Reference Compound (b) | 23 |

TEST EXAMPLE 2

The compounds of this invention, (1), (2), (3), (4) and (5), were diluted with acetone to a predetermined concentration, and 0.5 μl of each solution was topically applied to the thorax of female adult WHO-strain houseflies (standard susceptible strain) with a microsyringe. The flies were placed in plastic cups each having a diameter of 11 cm in which a bait (3% sugar water) was placed. 24 hours later, the alive and dead was evaluated to determine the $LD_{50}$ (median lethal dose) (μg/housefly). The results are shown in Table 4.

TABLE 4

| Compound | $LD_{50}$ (μg/housefly) |
|---|---|
| Compound (1) | 0.18 |
| Compound (2) | 0.13 |

TABLE 4-continued

| Compound | $LD_{50}$ ($\mu$g/housefly) |
| --- | --- |
| Compound (3) Reference | 0.10 |
| Compound (a) | 0.35 |
| Compound (4) | 0.038 |
| Compound (5) Reference | 0.042 |
| Compound (b) | 0.15 |

TEST EXAMPLE 3

10 to 15 female adult carmine mites were placed on each leaf of potted kidney beans (2-leaf stage) 9 days old after seeding. After standing in a constant temperature room at 27° C. for a week, a lot of mites in various growth stages were observed on the beans. Each of the emulsifiable concentrates prepared from the compounds of this invention, (1), (2), (3), (4), and (5), in the procedures described in Formulation Example 2 was diluted 500-fold with water and sprayed to the beans on a turntable in a proportion of 10 ml/pot. After 10 days, damage of the kidney beans by the mites was hardly observed.

While the invention has been described in detail and with reference to specific embodiments thereof, it will be apparent to one skilled in the art that various changes and modifications can be made therein without departing from the spirit and scope thereof.

What is claimed is:

1. A method for preparing an optically active α-cyano-3-phenoxybenzyl-2-(4-substituted-phenyl)isovalerate of the formula:

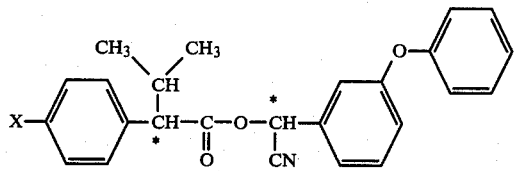

wherein X is a methoxy group which may be unsubstituted or substituted with a fluorine atom or atoms, or an ethoxy group which may be unsubstituted or substituted with a fluorine atom or atoms, and * indicates an asymmetric carbon atom, comprising (S)-α-cyano-3-phenoxybenzyl (S)-2-(4-substituted-phenyl)isovalerate, substantially free of other isomers, which method comprises crystallizing said compound from a solution of the compound of said formula having an (S)-configuration on the acid moiety with or without being seeded with crystals in the presence or absence of a basic catalyst, and separating the crystal of said compound from the mother liquor.

2. The method according to claim 1, wherein the crystallization is carried out in the presence of a basic catalyst.

3. A method for preparing an optically active α-cyano-3-phenoxybenzyl 2-(4-substituted-phenyl)isovalerate of the formula:

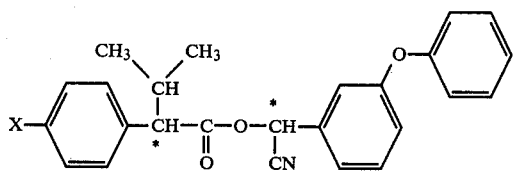

wherein X is a methoxy group which may be unsubstituted or substituted with a fluorine atom or atoms, or an ethoxy group which may be unsubstituted or substituted with a fluorine atom or atoms, and * indicates an asymmetric carbon atom, containing at least 60% of an (S)-α-cyano-3-phenoxybenzyl (S)-2-(4-substituted-phenyl)isovalerate, which method comprises crystallizing said compound from a solution of the compound of said formula having an (S)-configuration on the acid moiety with or without being seeded with crystals in the presence of a basic catalyst, and recovering the crystal of said compound together with the compound of said formula having an (S)-configuration on the acid moiety contained in the mother liquor.

4. The method according to claim 2 or 3, wherein said basic catalyst is a nitrogen-containing base.

5. The method according to claim 4, wherein said nitrogen-containing base is ammonia or triethylamine.

6. The method according to claim 1 or 3, wherein a solvent selected from the group consisting of a lower alcohol, an aliphatic hydrocarbon, an alicyclic hydrocarbon, a mixture thereof, and a solvent containing at least one of these solvents is used as a solvent for the crystallization.

7. The method according to claim 6, wherein said lower alcohol is methanol.

8. The method according to claim 1 or 3, wherein the process is characterized by seeding with crystals.

9. The method according to claim 1 or 3, wherein the crystallization is carried out continuously or semicontinuously.

10. The method according to claim 1 or 3, wherein X is a methoxy group.

11. The method according to claim 1 or 3, wherein X is a difluoromethoxy group.

* * * * *